United States Patent [19]

Honig et al.

[11] 4,152,373

[45] May 1, 1979

[54] PROCESS FOR PREPARING DIARYL METHYLPHOSPHONATE AND DERIVATIVES THEREOF

[75] Inventors: Milton L. Honig, Bronx; Edward D. Weil, Hastings-on Hudson, both of N.Y.

[73] Assignee: Stauffer Chemical Company, Westport, Conn.

[21] Appl. No.: 615,321

[22] Filed: Sep. 22, 1975

[51] Int. Cl.$^2$ ................................................ C07F 9/40
[52] U.S. Cl. .................................. 260/969; 260/953; 260/982; 260/984
[58] Field of Search ........................ 260/969, 967, 961

[56] References Cited

PUBLICATIONS

Arbuzov et al, English Translation of "Bull. Acad. Soci, U.S.S.R., Div. Chem. Sci.", 1954, pp. 361–367.

*Primary Examiner*—Anton H. Sutto
*Attorney, Agent, or Firm*—William R. Robinson

[57] ABSTRACT

A process is provided for the preparation of diaryl methylphosphonates through the reaction of triaryl phosphites with methanol in the presence of a catalytic quantity of methyl iodide. The reaction is conducted at a temperature of from about 170° C. to about 250° C. New and useful derivatives are produced by reaction of the diaryl methylphosphonates with polyols or amines.

9 Claims, No Drawings

PROCESS FOR PREPARING DIARYL METHYLPHOSPHONATE AND DERIVATIVES THEREOF

BACKGROUND OF THE INVENTION

Diaryl methylphosphonates and methods for their preparation have long been known in the art. Inter alia, Michaelis et al., Ber. 31, 1048 (1898); Morgan et al., J. Am. Chem. Soc., 74, 4526 (1952); Landauer et al., J. Am. Chem. Soc., 1953, 2224; and Behrman et al., J. Org. Chem., 35, 3063 (1970) all disclose the preparation of diphenyl methylphosphonate. The prior art method involves the reaction of methyl iodide with triphenyl phosphite to form a phosphonium iodide intermediate which is subsequently decomposed by alcohols or aqueous caustic to form diphenyl methylphosphonate. This earlier reaction is characterized by the use of a relatively large ratio (at least one molar equivalent) of costly methyl iodide and relatively low yields, generally less than 70%.

It is believed that these factors have reduced the commercial potential of diphenyl methylphosphonate and other diaryl methylphosphonates in spite of the fact that these compounds have long been known as useful intermediates in the preparation of various other compounds. For example, Coover et al., in U.S. Pat. No. 2,682,522, disclose the reaction of diphenyl methylphosphonate with dihydroxy-aromatics to provide polymeric organophosphonates.

Related compounds have also been disclosed in the art wherein the methyl group is replaced by other aliphatic or aromatic groups. These related compounds are usually prepared through the employment of similar reactions. In German Offenlegungsschrift No. 2,158,765 (1971), ethylene glycol is reacted with triphenyl phosphite in the presence first of a catalytic amount of alkali metal alkoxide (formed from e.g. sodium metal plus glycol) and then a catalytic amount of an alkali metal iodide to form a bis phosphonate at temperatures in the range of 220°–240° C. However, as described in this application in detail, this process is done stepwise and phenol is first distilled off taking advantage of the high boiling glycol. It would be expected that this process would fail with an alcohol boiling well below phenol, and it is probably no oversight that the cited German reference is limited to glycols, all of which are high boiling.

In accordance with the present invention, it has been surprisingly found that diaryl methylphosphonates can be effectively prepared in high yield through the reaction of the corresponding triaryl phosphite with methanol in the presence of a catalytic amount of methyl iodide at a temperature from about 170° C. to about 250° C.

The process of this invention can be characterized by the following reaction diagram:

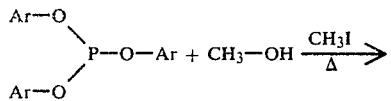
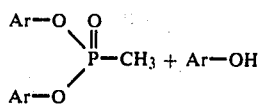

The term aryl as used herein and represented above as Ar—, is intended to include aryl radicals containing from 6 to about 14 carbon atoms inclusive. Illustrative of compounds included within this definition are phenyl, naphthyl, anthracyl, phenanthryl and the like.

Also included within this definition are aryl radicals which are substituted by non-interfering substituents such as alkyl, phenyl, chloro, bromo, alkoxy, aryloxy, alkylthio, arylthio, cyano, nitro and hydroxy.

By way of further illustrations of compounds falling within the definition of aryl, the following radicals are exemplary:
tolyl
xylenyl
chlorophenyl
t-butylphenyl
methoxyphenyl
phenoxyphenyl
phenylphenyl
benzylphenyl
methylthiophenyl
isopropylthiophenyl
cyanophenyl
nitrophenyl
mesityl.

The term "catalytic amount" as used herein means from about 0.1 to about 10% by weight based on the triaryl phosphite. Amounts from about 0.5 to 5% by weight are generally employed.

The reactants can be employed in stoichiometric amounts or in a ratio of from about 2:1 to 1:2 parts triaryl phosphite to methanol. For best yields, however, it is preferred to employ methanol in slight excess over stoichiometric.

Temperatures employed in this reaction are from about 150° C. to 300° C. While superatmospheric pressures can be employed in the reaction of the present invention, it can be effectively conducted at atmospheric pressure. This appears to be quite unexpected in view of the volatility of methanol and the reaction temperatures employed.

It has been additionally found that diphenyl methylphosphonate can be reacted with aliphatic polyols to provide useful and in some instances novel compositions.

Suitable polyols include pentaerythritol, di-(pentaerythritol), neopentylene glycol, trimethylolpropane, di(trimethylolpropane), glycerine, and the like.

These derivatives can be prepared by heating the reactants at a temperature of from about 170° C. to about 250° C. in the presence of a suitable catalyst such as magnesium chloride.

These compositions, all of which are useful as flame retardants for polymers can be represented by the following formulas:

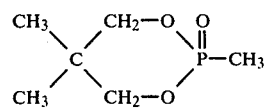

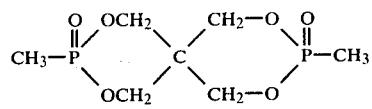
II.

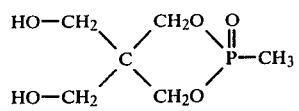
III.

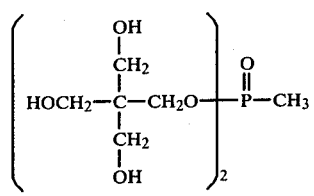
IV.

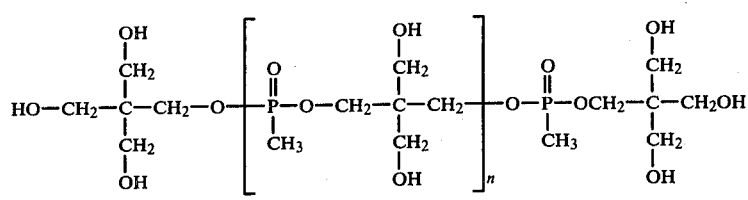
V.

wherein n=1 to 10, and the chain can be straight or branched.

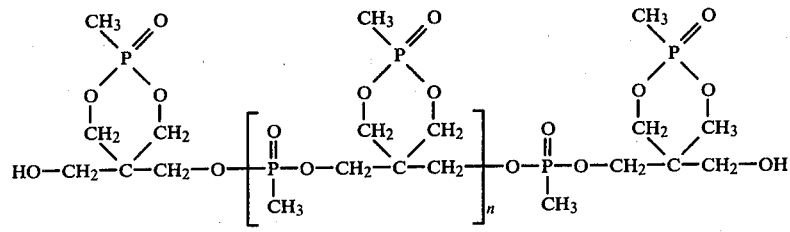
VI.

It will be appreciated that compounds II–IV and resins V–VI above are generally prepared in admixture, by reacting diphenyl methylphosphonate with pentaerythritol in various ratios. Analogous mixtures are prepared using dipentaerythritol or mixtures thereof with pentaerythritol. These phosphonate products, as mentioned, are flame retardants for plastics, textiles, and coatings. They also show surprising properties as smoke suppressants agents in these substrates.

EXAMPLE 1

A reactor fitted with an efficient condenser, thermometer, mechanical stirrer and side-arm addition funnel was charged with 1552 g (5.0 mol) of triphenyl phosphite. The reactant was placed under a nitrogen blanket and heated to reflux. A solution of 5.0 g of methyl iodide in 160 g (5.1 mol) of methanol was then slowly added over a two hour period. Throughout the addition, the temperature of the reactor contents was maintained within the 200°–250° C. range. One further hour at 215° C. proved sufficient for the reaction to reach completion. Subsequently, an aspirator vacuum distillation removed 468 g (5.0 mol) of phenol containing a small amount of anisole. Thereafter, a high vacuum distillation recovered 1150 g (4.6 mol, 92% yield) of diphenyl methylphosphonate. Glc analysis using a 6 foot column packed with 10% OV-101 on chromosorb W, was employed to monitor the progress of both the reaction and distillation. The 31P signal for the product appeared at −24.0 ppm. Proton nmr signals were seen at $\tau 8.36$ (3 H, doublet, J=18 HZ, CH$_3$P) and $\tau 2.9$–2.5 (10 H, multiplet, phenyl).

Anal. Calcd. for $C_{13}H_{13}O_3P$: C, 62.90; H, 5.27; P, 12.47. Found: C, 62.79; H, 5.27; P, 12.26.

EXAMPLES 2–6

In a manner similar to that described in Example 1 above, other triaryl phosphites were reacted with methanol in the presence of methyl iodide catalyst as indicated in the table below:

| Triaryl Phosphate Used | Diaryl Methyl-phosphonate Produced | Product Characteristics bp(° C./mm) | mp(° C.) | Yield (%) |
|---|---|---|---|---|
| 2 tris(p-tolyl) | di(p-tolyl) | 171/0.20 | viscous liquid | 56 |
| 3 tris(m-tolyl) | di(m-tolyl) | 145–147/0.15 | viscous liquid | 53 |
| 4 tris(p-chlorophenyl) | di(p-chlorophenyl) | 157–160/0.03 | viscous liquid | 34 |

-continued

| Triaryl Phosphate Used | Diaryl Methyl-phosphonate Produced | Product Characteristics bp(° C./mm) | mp(° C.) | Yield (%) |
| --- | --- | --- | --- | --- |
| 5-tris(p-tert-butylphenyl) | di(p-tert-butylphenyl | 174/0.07 | viscous liquid | 61 |
| 6 tris(p-methoxy-phenyl) | di(p-methoxy-phenyl) | 177–179/0.03 | 65–67 | 72 |

EXAMPLE 7

The following ingredients were charged to a reaction vessel:

| Ingredient | Amount in grams | Mols |
| --- | --- | --- |
| Diphenyl methylphosphonate | 173.6 | 0.70 |
| p-tert-butylphenol | 105.0 | 0.70 |
| Magnesium chloride | 1.0 | — |

This mixture was heated to a temperature of from 187° C. to 194° C. for a period of 8.5 hours. After this reaction period, the reaction vessel was subjected to a vacuum of 40 mm Hg. and 74 grams of volatiles were removed by distillation at this reduced pressure. Greater than 90% of the removed volatiles proved to be phenol.

The reaction vessel was then subjected to a vacuum of 0.8 mm Hg and the product was removed by distillation. The distillate fraction boiling in the range from 167° C. and 212° C. provided 194 grams of a water-white liquid product in 92% yield.

Analysis by gas chromatograph revealed three components in the recovered product. These were identified as follows:

(1) diphenyl methylphosphonate
(2) p-t-butylphenyl phenyl methylphosphonate
(3) di(p-t-butylphenyl) methylphosphonate These components were present in a ratio of 1:2:1 respectively. As the mixture is a liquid, it is useful as a thermally stable functional fluid and plasticizer.

EXAMPLE 8

A vessel fitted with cold finger-distillation head, thermometer and mechanical stirrer was charged with 136 g (1.0 mol) of pentaerythritol. Residual water contained in the pentaerythritol was removed by azeotropic distillation with 150 ml of benzene. The reactor was then further charged with 496 grams (2.0 mols) of diphenyl methylphosphonate and 0.8 grams of MgCl$_2$. These reactants were slowly heated under nitrogen to a temperature of 190° C. and maintained at this temperature for a period of 4 hours. Phenol totaling 340 g (3.6 mols) was removed by distillation (bp 105° C./25 mm). A pump vacuum of 0.7 mm was applied for a final 2 hours at 200° C. pot temperature to remove all volatiles. The molten product was poured into an aluminum foil sheet to cool. A clear brittle solid weighing 262 grams remained. Pulverization of the solid in a blender gave a white powder of mp 100°–105° C. Its phosphorus content was 22.4%. An acid number of 56 mg KOH/g was noted in water using naphtholbenzein as indicator.

This product at 7.5 parts per hundred in poly(ethylene terephthalate) gave a limiting oxygen index of 29.6 as compared to 20.8 for the unmodified polyester.

EXAMPLE 9

Pentaerythritol (136 g, 1.0 mol) was placed into a reactor. Residual water was removed by azeotropic distillation with benzene. Then, 421 g (1.7 mol) of diphenyl methylphosphonate along with 1.0 g MgCl$_2$ were added to the reactor. The contents were heated to a temperature of 150°–170° C. and maintained for a period of 10 hours. Thereafter, 314 grams (3.3 mols) of phenol were removed by distillation at 91°/16 mm. A final stripping was conducted at 0.8 mm with the pot temperature at 190° C. for a 4 hour period. The molten product was poured onto aluminum foil to cool. The resultant brittle solid weighing 232 g was ground into a white powder of mp 79°–95° C. An acid number of 10 mg KOH/g was noted in water using naphtholbenzein as indicator. The hydroxyl number was 147 mg KOH/g, while the phosphorus content was 21.6%.

EXAMPLE 10

Pentaerythritol (136 g, 1.0 mol), dried by the benzene azeotrope procedure, 372 g (1.5 mol) of diphenyl methylphosphonate and 1.0 g MgCl$_2$ were heated together at 180°–190° C. over a 10 hour period. Thereafter, phenol totaling 259 g (2.75 mol) was removed by distillation under a 45 mm vacuum. Final stripping was done at 1.5 mm and 190° C. for 5 hours. The product was poured molten into aluminum foil and allowed to cool. Obtained were 232 g of a pale yellow, brittle solid that was readily ground to a white powder of mp 65°–70° C. This material had an acid number of 8.4 mg KOH/g, a hydroxyl number of 209 mg KOH/g and contained 20.2% phosphorus.

EXAMPLE 11

Pentaerythritol 136 g. (1.0 mol), dried by the benzene azeotrope procedure, 248 g (1.0 mol) of diphenyl methylphosphonate and 1.0 g MgCl$_2$ were heated together at 165°–180° C. over a 12 hour period. Subsequently, phenol weighing 178 g (1.9 mol) was removed by distillation under a 40 mm vacuum. Final stripping was done at 5 mm and 175° C. for 4 hours. The product was poured molten onto aluminum foil and allowed to cool. Obtained were 184 g of a sticky pale yellow resin. This material exhibited an acid number of 10.3 mg KOH/g, a hydroxyl number of 345 mg KOH/g and contained 15.4% phosphorus.

EXAMPLE 12

Into a flask were placed 127 g (0.5 mol) of dried dipentaerythritol, 248 g (1.0 mol) of diphenyl methylphosphonate and 1.0 g of AlCl$_3$. These compounds were heated together for 9 hours at a temperature of 190°–209° C. Afterwards, phenol weighing 170 g was recovered by distillation using an aspirator vacuum. The residual contents of the reactor were poured while hot onto aluminum foil. Once cool, the product (171 g) was ground in a blender to a white powder having a melting point of 145°–150° C. An acid number of 31 mg KOH/g was observed for this material.

This product, when incorporated at 10 parts per hundred into an epoxy resin (diglycidyl ether of bisphenol A cured by triethylene tetramine) afforded a reduction of the smoke level, as measured in the National Bureau of Standards Smoke Chamber, to approximately 50% of the level of the unmodified epoxy resin, and also caused the resin to be self-extinguishing.

EXAMPLE 13

A reactor was charged with 31.2 g (0.30 mol) of dry neopentylene glycol, 74.4 g (0.30 mol) of diphenyl methylphosphonate and 0.4 g of MgCl₂. This mixture was heated for a period of 6 hours at a temperature of 210°–215° C. Subsequent vacuum distillation afforded 54 g of phenol. In addition, 16 g (0.10 mol) of 5,5,-dimethyl-2-oxo-2-methyl-1,3,2-dioxaphosphorinane was obtained having a boiling point of 128°–130° C./3.4 mm, Hg. Upon standing, this product solidified. Recrystallization from benzene-heptane, gave white crystals having a melting point of 119°–121° C. The H-nmr scan of this product exhibited signals at τ8.95 (3H, singlet, CH₃C), τ8.88 (3H, singlet, CH₃C), τ8.42 (3H, doublet, τ=17.5 Hz, CH₃P) and τ6.4–5.6 (4H, doublet of quartets, CH₂O).

EXAMPLE 14

Di(trimethylolpropane) (125 grams, 0.50 mol), diphenyl methylphosphonate (248 grams, 1.0 mol) and 1 gram of MgCl₂ were heated together at a temperature of 175°–180° C. for a period of 3 hours and then at 198° C. for another 7 hours. Phenol was removed by a 30 mm Hg vacuum distillation and totaled 166 grams. A further 27.6 grams of volatiles were distilled using a 0.5 mm vacuum (pot temperature was 195° C.). The molten product was poured onto aluminum foil to cool. A sticky semi-solid weighing 187 grams was obtained whose phosphorus content was 15.9%.

The diaryl methylphosphonates of the present invention are useful as intermediates in reactions for producing methylphosphonamides and methylphosphonamidates. These nitrogen containing products are useful as flame retardants for plastics, textiles and coatings.

The reactions are conducted by heating at a temperature from about 150° C. to about 250° C. a diaryl methylphosphonate with compounds to the type RR'NH where R and R' are the same or different and are hydrogen, alkyl, substituted alkyl, aryl, substituted aryl, alkylene or arylene. An acid catalyst can be used as an option. Heating is maintained until one or two molar equivalents of the phenol corresponding to the aryl groups are released. The products have the following general structure:

CH₃P(O)(Y)(NRR')

In the foregoing structure, Y can be O—Ar or NRR'. When the R' group is hydrogen, further condensation reactions can be carried out to produce products of the following structures:

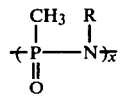

where x is greater than or equal to 2 or

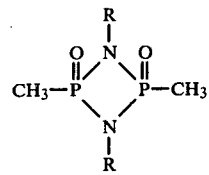

When the amine employed is a diamine, a hydroxyalkylamine or a hydroxyarylamine, oligomeric and polymeric methylphosphonamides and methylphosphonamidates may be obtained.

The following examples further illustrate the foregoing.

EXAMPLE 15

A reaction vessel fitted with thermometer, distillation head and mechanical stirrer was provided with 124 g (0.5 mol) of diphenyl methylphosphonate, 30 g (0.5 mol) of ethylenediamine and 0.5 g of MgCl₂. The vessel was sealed and placed under a nitrogen atmosphere. Heat was applied. A temperature of 190°–205° C. was reached and maintained for 11 hours. Phenol was subsequently removed under an 18 mm vacuum. This distillate amounted to 94.8 g of which 16% was unreacted ethylenediamine (0.25 mol). The product was a tan residue. While hot, the product was poured onto aluminum foil to cool. The resultant solid was easily pulverized to a pale yellow powder having a melting point of 102°–110° C. Its acid number in water was 1.12 mg KOH/g toward a methyl red indicator. Elemental analysis indicated that 24.8% phosphorus and 14.0% nitrogen was present in the product.

EXAMPLES 16–19

Further ethylenediamine-diphenyl methylphosphonate aminolysis experiments were performed to evaluate the effects of reactant ratio and catalyst on the nature of the product. The Table 16–19 below lists said experiments.

TABLES 16–19

| | Reaction Profile | | | | Product Analysis | | | | |
|---|---|---|---|---|---|---|---|---|---|
| EXAMPLE | Molar Ratio (ArO)₂P(O)Me:H₂NC₂H₄NH₂ | Catalyst | Reaction Time (in.) | Maximum Temp. (° C.) | Product Yield (g) | % P | % N | MP (° C.) | Acid No. |
| 16 | 3.0:3.0 | MgCl₂ | 10 | 215 | 350 | 20.3 | 10.5 | 68–71 | 4.0 |
| 17 | 1.0:2.0 | MgCl₂ | 12 | 206 | 94 | 27.6 | 12.3 | 118–130 | 50 |
| 18 | 0.5:0.5 | AlCl₃ | 11 | 200 | 45 | 26.8 | 15.8 | 137–148 | 4.5 |
| 19 | 0.2:0.1 | MgCl₂ | 9 | 200 | 13 | 21.0 | 10.9 | — | — |

EXAMPLE 20

A reactor was provided with 1,3-diaminopropane (13.2 g, 0.18 mol), diphenyl methylphosphonate (74.4 g, 0.30 mol) and 0.1 g AlCl₃. The reactor was sealed and placed under a nitrogen atmosphere. Heat was applied and the temperature was maintained at 200°–213° C. for 8 hours. Thereafter, 23.9 g of phenol was removed by distillation under 10 mm vacuum. For a final devolatilization, a pump vacuum of 0.04 mm was applied in conjunction with a 210°–230° C. pot temperature. Another 32.6 g of volatiles were thus removed. The molten product was poured onto aluminum foil for cooling. A light brown, brittle solid was obtained weighing 16 g. It melted at 100°–110° C. The phosphorus and nitrogen contents of the product were 25.9% and 14.1%, respectively.

EXAMPLE 21

A reactor was provided with 1,4-diaminobutane (13.2 g, 0.15 mol), diphenyl methylphosphonate (74.4 g, 0.30 mol) and 0.1 g $AlCl_3$. The reactor was sealed and placed under a nitrogen atmosphere. Heat was applied and temperature was maintained at 197°–224° C. for 10 hours. Subsequently, 17.3 g of phenol was removed by distillation under a 10 mm vacuum. Final devolatilization was accomplished under a 0.03 mm vacuum at approximately 115° C. over an 8 hour period. Another 54.2 g of volatiles were recovered. The molten reactor contents were then poured onto aluminum foil to cool. A brown brittle solid weighing 11.0 g and having a melting point of 85°–100° C. was obtained. Phosphorus and nitrogen contents of the product were 25.1% and 11.4%, respectively.

EXAMPLE 22

A reactor containing 46.4 g (0.40 mol) of hexamethylene diamine, 99.2 g (0.40 mol) of diphenyl methylphosphonate and 0.1 g of $MgCl_2$ was heated for 12 hours at 200° C. Phenol totaling 52 g was removed by distillation at 18 mm. The molten product was poured onto aluminum foil to cool. A brown, tacky solid weighing 80 g was recovered. The melting point was 52°–55° C.

EXAMPLE 23 p-Phenylenediamine (32.4 g, 0.30 mol), diphenyl methylphosphonate (74.4 g, 0.30 mol) and 0.3 g of $MgCl_2$ were heated together at 140°–212° C. over a 5 hour period. Volatiles were then removed by distillation under a 25 mm vacuum. These volatiles weighed 46.2 g and consisted of phenol and excess p-phenylenediamine. The pot residue, while still molten, was poured onto aluminum foil to cool. A brown, brittle solid weighing 55 g was obtained having a melting point at 82°–87° C. Phosphorus content of the product was 14.0%.

EXAMPLE 24 m-Phenylenediamine (32.4 g, 0.30 mol), diphenyl methylphosphonate (74.4 g, 0.30 mol) and 0.3 g of $MgCl_2$ were heated together at 200° C. over a 6 hour period. Vacuum distillation (25 mm) was then used to remove 64 g of volatiles consisting mainly of phenol and unreacted m-phenylenediamine. The molten product was poured onto aluminum foil to cool. A brittle maroon solid weighing 36.8 g was obtained.

EXAMPLE 25

The product of Example 15 was padded from a 25% aqueous solution onto a 50:50 cotton-polyester blend. It was cured at 350° F. for 3 minutes. The weight increase of the fabric indicated a dry add-on of 19.8% Analysis showed that 4.3% P and 2.46% N were present. A standard vertical char test was then performed. Char length was 1.75 inches.

EXAMPLES 26

The excellent thermal stability characteristics of many of the aforementioned oligomers account for their usefulness as flame retardants in polymers requiring high temperature processing. Poly(ethylene terephthalate) is an example of a high temperature processed polymer. It served as a screening substrate for the compounds mentioned herein. Polymer compositions were prepared by hand mixing usually 7.5 phr of flame retardant with non-flame retarded polyester at 290°–300° C. These were drawn by suction into a 6 mm diameter Teflon tube for casting into rods. Flammability was measured by the Limiting Oxygen Index method described by Fenimore and Martin, *Modern Plastics*, Nov., 1966, p. 141 and Isaacs, *Modern Plastics*, March, 1970, p. 124, wherein the minimum percent oxygen to sustain candle-like burning on a vertical rod is determined.

The results were as follows:

| MATERIAL EVALUATED | LIMITING OXYGEN INDEX (7.5 ph) |
| --- | --- |
| Control | 20.6 |
| Example 15 product | 32.1 |
| Example 23 product | 30.8 |
| Example 24 product | 31.7 |
| Example 12 product | 29.6 |

Having set forth the general nature and some examples of the present invention, the scope is now particularly set forth in the appended claims.

What is claimed is:

1. A process for preparing diaryl methylphosphonate which comprises reacting the corresponding triayl phosphite with methanol in the presence of a methyl iodide catalyst, said catalyst being employed in an amount of from about 0.5% to about 5% by weight based on the triaryl phosphite, at a temperature of from about 170° C. to about 250° C.

2. The process of claim 1 wherein the methyl iodide is employed in an amount of from about 1% to about 3% by weight methyl iodide.

3. The process of claim 1 wherein the diaryl methylphosphonate is diphenyl methylphosphonate.

4. The process of claim 1 wherein the triaryl phosphite employed is tris-p-tolyl phosphite.

5. The process of claim 1 wherein the triaryl phosphite employed is tris-m-tolyl phosphite.

6. The process of claim 1 wherein the triaryl phosphite employed is tris(p-chlorophenyl)phosphite.

7. The process of claim 1 wherein the triaryl phosphite employed is tris(p-tert-butylphenyl)phosphite.

8. The process of claim 1 wherein the triaryl phosphite employed is tris(p-methoxyphenyl)phosphite.

9. The process of claim 1 wherein the triaryl phosphite employed is triphenyl phosphite.

* * * * *